United States Patent [19]

Woods et al.

[11] Patent Number: 4,640,849
[45] Date of Patent: Feb. 3, 1987

[54] META-BRIDGED STYRYLOXY RESINS

[75] Inventors: John G. Woods, Dublin; John M. Rooney, Kildare, both of Ireland

[73] Assignee: Loctite (Ireland) Limited, Dublin, Ireland

[21] Appl. No.: 824,903

[22] Filed: Jan. 31, 1986

[51] Int. Cl.$^4$ .............. B05D 3/06; C08F 283/04; C08F 26/02; C08G 18/08; C07C 125/06
[52] U.S. Cl. .............. 427/54.1; 525/455; 526/301; 526/312; 526/313; 528/49; 528/110; 560/25; 560/61; 560/158; 568/631; 568/646; 522/6; 522/31; 522/32
[58] Field of Search .............. 427/54.1; 525/455; 526/301, 312, 313; 528/49, 110; 560/25, 61, 158; 568/631, 646

[56] References Cited

U.S. PATENT DOCUMENTS

| | | | |
|---|---|---|---|
| 3,327,019 | 6/1967 | Mylenbusch et al. | 525/44 |
| 4,145,479 | 3/1979 | Adams et al. | 428/500 |
| 4,486,582 | 12/1984 | Hefner, Jr. | 526/301 |
| 4,543,397 | 9/1985 | Woods et al. | 525/455 |

OTHER PUBLICATIONS

Chemical Abstracts, 63: 9968c, (1965).
Goka et al., Polymer, 16, 819–826, (1975).
Cotrel et al., Macromolecules, 9, 931–936, (1976).
Ito et al., Macromolecules, 16, 510–517, (1983).

Primary Examiner—Thurman K. Page
Attorney, Agent, or Firm—Walter J. Steinkraus; Eugene F. Miller

[57] ABSTRACT

Polyfunctional cationically polymerizable styryloxy compounds of the formula

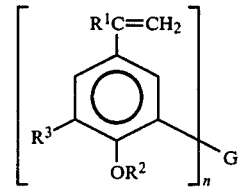

where $R^1$ is H or methyl; $R^2$ is hydrocarbyl, hydrocarbyl interrupted by ether oxygen atoms, or halo substituted hydrocarbyl; $R^3$ is H, lower alkyl, or alkoxy; G is any multivalent organic or inorganic radical free of amino or aliphatic thiol groups; and n is an integer of two or more.

20 Claims, No Drawings

META-BRIDGED STYRYLOXY RESINS

FIELD OF THE INVENTION

It is an object of the present invention to provide a new class of polymerizable monomers which are polyfunctional, so as to be cured to cross-linked high molecular weight polymer networks, and which are readily cationically polymerizable.

BACKGROUND OF THE INVENTION

In USSR Pat. Nos. 443874 and 478026 there are described ion exchange polymers prepared by free radical copolymerization of styrene or maleic anhydride, respectively, with p-glycidoxy-α-methyl styrene (I)

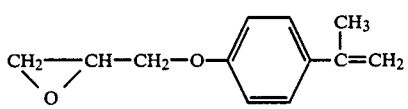

In U.S. Pat. No. 3,327,019 there are described diethers which are the reaction product of p-glycidoxy styrenes and polyols. These compounds include aliphatic hydroxyl groups.

In Macromolecules, 16, 510–517(1983), there is described the cationic polymerization of p-methoxy and p-(ethoxymethoxy)-α-methyl styrenes with boron trifluoride etherate as initiator in dichloromethane. These polymers are then subjected to ether cleavage reactions to yield linear polymers containing pendant phenolic groups.

It is known from kinetic studies of the cationic polymerization of p-methoxy styrene that this monomer has a very high rate of polymerization. See, e.g., Macromolecules, 9, 931–936(1976); and Polymer, 16, 819–826(1975).

SUMMARY OF THE INVENTION

The present invention is directed to a new class of cationic polymerizable monomers. In common with the monofunctional monomers discussed above, the inventive monomers contain styryloxy(p-vinylphenol ether) functionality. They are represented by the formula:

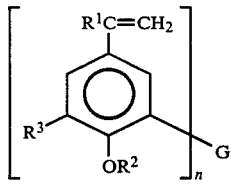

where $R^1$ is H or methyl; $R^2$ is hydrocarbyl, hydrocarbyl interrupted by ether oxygen atoms, or halo substituted hydrocarbyl; $R^3$ is H, lower alkyl, or alkoxy; G is any multivalent organic or inorganic radical free of amino or aliphatic thiol groups; and n is an integer of two or more.

In addition to high reactivity to cationic polymerizations, the inventive monomers have been shown to develop an intense coloration when they are polymerized by UV radiation in the presence of acid generating photoinitiator. Under some circumstances this coloration is sufficient to mask a substrate, providing a useful means of generating opacity in photocurable coatings. This coloration is also observed in chemically initiated cationic polymerizations of these materials.

An additional feature of solid polyfunctional styryloxy resins of the invention is an ability of these resins to cure by UV irradiation without added photoinitiator. This cure is believed to involve a radical mechanism.

DETAILED DESCRIPTION OF THE INVENTION

The inventive monomers may readily be prepared from p-alkoxy-m-hydroxy styrenes or similarly substituted α-methyl styrenes by a variety of methods such as etherification with an appropriate multifunctional etherifying agent or reaction with multifunctional epoxies. Additionally, unlike the p-bridged styryloxy monomers of U.S. Pat. No. 4,543,397, meta-bridged styryloxy monomers of the present invention may also be prepared by direct reaction of meta hydroxy groups with isocyanates or acid chlorides. The resulting meta urethane or ester groups do not interfere with the cationic curability since the molecule retains the p-ether functionality which is critical to cationic curability.

As an alternative to reaction of substituted styrenes as discussed above, a multifunctional meta-bridged aromatic molecule may be formed having an ether group ($OR^2$) ortho to the bridge and a group para to the ether which may be converted to a vinyl or isopropenyl group.

Wittig reaction on meta bridged p-alkoxy acetophenones or phenaldehydes, using methyl triphenylphosphonium bromide is one such conversion procedure. A similar procedure using similarly substituted halomethyl benzenes to prepare triphenyl phosphonium salts followed by reaction with formaldehyde, may also be used. This latter procedure is similar to that described in U.S. Pat. No. 4,412,050, modified by the halobenzene used, which is incorporated herein by reference.

The range of suitable bridging groups G is broader than the bridging groups suitable for the p-bridged styryloxy resins described in U.S. Pat. No. 4,543,397. Direct hydrocarbyl linkages to the aromatic ring are possible as are ester or urethane linkages obtained by reaction of a meta hydroxyl group with esterifying agents, such as acids, acid chlorides or anhydrides, or isocyanates. Further, although it is known that aliphatic hydroxyls are known to the art as chain transfer agents for cationic polymerizations, and so retard such polymerizations, such reactivity does not preclude the presence of aliphatic hydroxyls in the bridging group G. Thus G may also be suitably formed by reaction of polyepoxides with meta hydroxyls. G however must not contain amino or thiol groups which, it is believed, will stop the polymerizations. Apart from this limitation, any n-functional radical may be employed as G including polyorganosiloxane, polyphosphazene, polyurethane, polyether, polyester, polythioether, polythioester, polyacrylic, polystyrene polyoxazolidone, polyimide and simple hydrocarbon radicals. G may also be a radical having a mixture of such functionalities.

In formula (II) above, it is generally preferred that $R^3$ is H, methyl, or methoxy. However, other lower alkyl or alkoxy (up to about $C_4$) may be included as substituents $R^3$.

Examples of $R^2$ groups are methyl, ethyl, t-butyl or other alkyl groups, alkenyl groups such as allyl and cycloaliphatic or aromatic hydrocarbons such as cyclohexyl, phenyl, tolyl, benzyl, etc. $R^2$ may also be a hydrocarbyl group interrupted by ether oxygen atoms such as 2-ethoxyethyl. Still further, $R^2$ may be halo substituted hydrocarbyl such as trifluoropropyl or 2-chloroethyl.

The preferred starting material for the inventive monomers is isovanillin. Isovanillin which has the formula

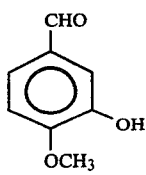

III is readily available, relatively cheap, already has the necessary p-ether functionality, can be easily bridged through the hydroxyl group and includes an aldehyde group which can be readily converted to vinyl by Wittig reaction as disclosed above and in the examples.

Polymerization of the inventive monomers may be accomplished by conventional acid and Lewis acid cationic initiators such as methane sulfonic acid, toluene sulfonic acid and boron trifluoride etherate. UV cationic initiators may also be used. Such UV cationic photoinitiators include salts of a complex halogenide having the formula:

$$[A]_b^+[MX_e]^{-(e-f)}$$

where A is a cation selected from the group consisting of iodonium, sulfonium, pyrylium, thiopyrylium and diazonium cations, M is a metalloid, and X is a halogen radical, b equals e minus f, f equals the valance of M and is an integer equal to from 2 to 7 inclusive, e is greater than f and is an integer having a value up to 8. Examples include di-p-tolyl iodonium hexafluorophosphate, diphenyl iodonium hexafluorophosphate, diphenyl iodonium hexafluoroarsenate and UVE 1014 (trademark of General Electric), a commercially available sulfonium salt of a complex halogenide.

Certain monomers, usually solids, will also undergo UV initiated polymerization in the solid state without initiator, yielding an essentially uncolored product. A radical mechanism is believed to be involved. This UV, initiator free, polymerization has also been obtained with a liquid silicone backbone resin of the invention.

The production of colored reaction mixtures by cationic initiators has been reported before for styryloxy monomers. Permanent coloration in the cured products of the invention is believed to result from particular termination reactions involving stable carbocations. The development of color can thus be controlled by selecting polymerization conditions designed to select for or against termination by stable carbocations. The development of permanent color is a result of polymerization termination reactions is especially advantageous at certain UV cured opaque coating applications where the use of pigments or dyes in the composition blocks UV, resulting in only surface cure of the coating. Since the inventive resins develop their intense coloration only after initiation of polymerization, initiation by UV is not interefered with.

The invention may be illustrated by reference to the following nonlimiting examples:

EXAMPLE 1

Isovanillin (76 g) was dissolved in a stirred mixture of potassium carbonate (104 g) and acetone (450 mls) followed by the dropwise addittion of allyl bromide (67 g) over ca. 20 mins. The mixture was refluxed for 5 hours, cooled and filtered. The solvent was removed from the filtrate under reduced pressure and the residue was distilled under vacuum to yield 3-allyloxy-4-methoxybenzaldehyde (85 g), b.p. 137°–150° C. at 1.5 mbar.

60 MHz, $^1$HMR (CDCl$_3$) $\tau$ 0.2 (s, 1H, CHO), $\tau$ 2.45–3.1 (m, 3H, ArH), $\tau$ 3.6–4.9 (m, 3H, CH=CH$_2$), $\tau$ 5.35, (d, 2H, OCH$_2$), $\tau$ 6.1 (S, 3H, OCH$_3$).

EXAMLE 2

Sodium amide (39 g) was dispersed in dry tetrahydrofuran (800 mls). Methyltriphenylphosphonium bromide (102 g) was added and the mixture stirred at R.T. for 2 hours. 3-allyloxy-4-methoxy-benzaldehyde (50 g) was then added dropwise over ca. 15 mins. and the mixture stirred for a further 3 hours. The mixture was filtered and the solvent removed from the filtrate under reduced pressure. The residue was washed with diethyl ether (1.5l) and the solvent removed to yield a brown coloured resin. The washing process was repeated and the residue obtained was distilled under reduced pressure to give 3-allyloxy-4-methoxystyrene (29.5 g), b.p. 98°–104° C. at 0.8 mbar.

60 MHz, $^1$HMR (CDCl$_3$) $\tau$ 2.45–4.90 (m, 9H, ArH+vinyl CH=CH$_2$+allyl CH=CH$_2$), $\tau$ 5.35 (d, 2H, OCH$_2$), $\tau$ 6.1 (S, 3H, OCH$_3$).

EXAMPLE 3

A solution of 3-allyloxy-4-methoxystyrene (13.3 g) and toluene (49 g) was prepared. To the stirred solution was added dihydrogen hexachloroplatinate (IV) hexahydrate (0.64 g of 2% solution in n-butyl acetate). The resulting solution was heated to 80° C. and a Si-H terminated polydimethylsiloxane resin (35.4 g) of molecular weight 1,010 was added gradually over 90 minutes. At the end of this time infra-red spectroscopy showed that the peak at 2130 cm$^{-1}$ had disappeared indicating complete consumption of the Si-H groups. Solvent was then removed under reduced pressure to yield 43.65 g of a cationically cureable liquid resin of the formula:

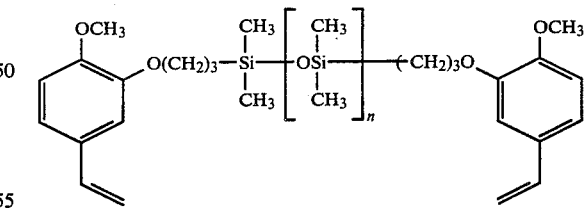

Reaction of one gram of this product with 0.02 g of methane sulfonic acid led to rapid formation of a rubbery gel insoluble in common organic solvents.

EXAMPLE 4

An aliquot of the difunctional styryloxy silicone resin prepared in Example 3 was blended with 4% by weight of a commercially available triarylsulfonium salt photoinitiator (UVE 1014, trademark of General Electric) and poured into an open-topped plastic cup (12 mm in diameter and 1.5 mm deep). The filled cup was then exposed to ultra-violet light from a Lumatec Superlite 201 containing a high pressure mercury arc, 5 mm from the end of a 1 m long fluid-filled light guide. After 90 secs. exposure, the composition had cured to a rubbery, deep red colored slug which did not dissolve on shaking with dichloromethane for three minutes.

EXAMPLE 5

Sebacoyl chloride (23.9 g) was added dropwise to a solution of isovanillin (30.4 g) in dry pyridine (150 mls). After 0.5 hours, the precipitated pyridine hydrochloride was removed by filtration through a bed of celite. The pyridine was removed from the filtrate under reduced pressure. The residue was taken up in dichloromethane (150 mls) and the solution washed with water (3×100 ml portions). The organic fraction was dried over sodium sulfate and the solvent removed under reduced pressure to give the crude ester which crystallized from a blend of toluene and petroleum spirit to yield 38 g. of a product with the formula:

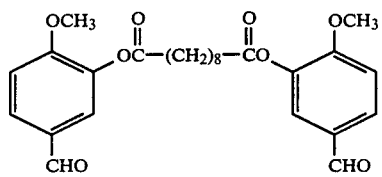

60 MHz, $^1$HMR (CDCl$_3$) $\tau$ 0.2 (S, 2H, CHO), $\tau$ 2.25–3.10 (m, 6H, ArH), $\tau$ 6.2 (S, 6H, OCH$_3$), $\tau$ 7.5 (t, 4H, COCH$_2$), $\tau$ 8.0–8.9 (m, 12H, —CH$_2$CH$_2$—).

EXAMPLE 6

Methyltriphenylphosphonium bromide (43 g) was added to a stirred suspension of sodium amide (5.1 g) in dry tetrahydrofuran (THF) (200 mls). After 1.5 hrs. a solution of the aldehyde prepared in Example 5, (23 g) in dry THF (60 mls) was added gradually and the mixture stirred for two hours at room temperature followed by a further 6 hours under reflux. The mixture was filtered and the solvent removed from the filtrate to give an organic residue. This material was dissolved in hot toluene and cooled to −18° C. A precipitate was formed which was filtered and toluene was removed to yield 30 grams of a cationically curable resin.

Addition of 0.02 g methane sulfonic acid to 1.0 g of this resin caused an exothermic reaction to occur which resulted in the formation of a red coloured, solvent insoluble, gel.

EXAMPLE 7

An aliquot of the resin prepared in Example 6 was blended with 5% by weight of cationic photoinitiator GE 1014 (trade mark of General Electric Co.) and smeared onto a glass slide to give an approximate 0.5 mm thick film. The film was exposed to ultraviolet light from a UVALOC 1000 lamp (trade mark of Loctite Deutschland) containing a medium pressure mercury arc lamp, 10 cms from the lamp source. After 60 seconds exposure, the film had cured to an organic solvent insoluble coating.

EXAMPLE 8

Isovanillin (15.2 g), diglycidyl ether of bis-phenol A (Epikote 828, Shell Co. trade name) (23.1 g) and benzyltrimethylammonium hydroxide (0.23 g) were heated together at 100° C. with stirring for 3.5 hours. On cooling, a solid like resin was obtained which was shown by gel permeation chromatography to consist principally of the dialdehyde product represented by the formula:

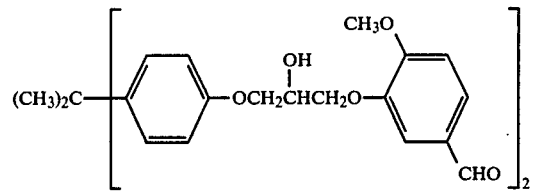

The resin also contained smaller amounts of higher molecular weight analogues directly corresponding to the distribution of molecular weights in the starting epoxide.

EXAMPLE 9

Methyltriphenylphosphonium bromide (40.2 g) was added to a stirred suspension of sodium amide (4.74 g) in dry THF (200 mls). After 1.5 hours, a solution of the aldehyde prepared in Example 8 (30.3 g), in dry THF (75 mls) was added gradually and the mixture stirred at room temperature for a further two hours. The mixture was then heated under reflux for two hours, filtered and the solvent removed under reduced pressure. The crude residue thus obtained was dissolved in hot ethanol and allowed to cool at −18° C. for several hours. A precipitate was formed which was filtered, washed with a little cold ethanol and dried. This material (19 g), which was shown by gel permeation and $^1$HMR spectroscopy to consist principally of the styryloxy derivative represented by the formula

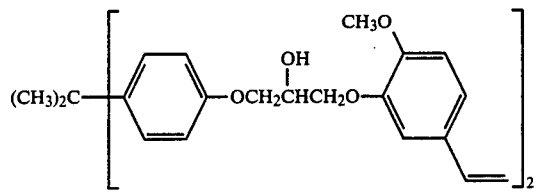

along with smaller amounts of higher molecular weight analogues and triphenylphosphine oxide, was cationically curable. Addition of 0.02 g of methane sulfonic acid to 1.0 g of the precipitated resin caused an exothermic reaction to occur, which resulted in the formation of a purple solid. This solid was found to be insoluble in dichloromethane.

EXAMPLE 10

An aliquot of the resin prepared in Example 9 was blended with 5% by weight of cationic photocatalyst GE 1014 (General Electric Co.) and smeared onto a glass slide to give a film approximately 0.5 mm in thickness. The film was exposed to ultraviolet light from a Lumatec lamp, as described in Example 4, for 60 secs. After this time, the film had converted to a dry, highly coloured, opaque coating which was insoluble in organic solvents.

EXAMPLE 11

Two equivalents of potassium carbonate are added slowly with stirring to a solution of 4-hydroxybenzaldehyde in acetone. A solution of allyl bromide (1.1 equivalent) in acetone is added and the mixture is refluxed for two hours, filtered to remove inorganic salts and volatiles stripped under reduced pressure. The resulting 4-allyloxybenzaldehyde is then heated for six hours at 220° C. to yield the rearrangement product, 3-allyl-4-hydroxybenzaldehyde. One equivalent of 3-allyl-4-hydroxybenzaldehyde is dissolved in acetone and two equivalents of potassium carbonate are added slowly with stirring followed by a solution of 1.1 equivalents of methyl iodide in acetone. This mixture is refluxed for several hours, filtered and stripped to yield 3-allyl-4-methoxybenzaldehyde.

The 3-allyl-4-methoxybenzaldehyde is then hydrosilated according to the procedure of Example 3 and a Wittig reduction on the aldehyde is performed according to the procedure of Example 6, yielding a cationically cureable difunctional meta-bridged styryloxy resin of the formula:

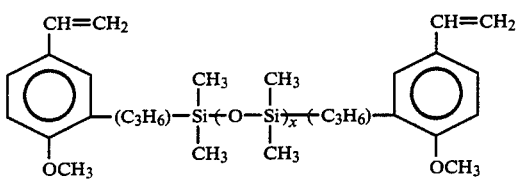

EXAMPLE 12

Methyltriphenylphosphonium bromide (352 g) was added to a stirred suspension of sodium amide (38.6 g) in dry THF (1.21). Over two hours, the mixture was stirred and dry nitrogen bubbled through the liquid. A solution of isovanillin (100 g) in dry THF (300 mls) was added gradually and the mixture heated under reflux for five hours. On cooling the solids were removed by filtration and the solvent distilled. The crude residue was dissolved in dichloromethane (1.01) and extracted with 0.8M sodium hydroxide solution (2×500 mls). The combined aqueous layers were carefully neutralized with dilute hydrochloric acid to pH 7 and extracted with dichloromethane (3×500 mls). The extracts were combined, dried (Na₂SO₄) and the solvent removed to yield 63 g of a mixture of phenols identified as comprising mainly 3-hydroxy-4-methoxy-styrene containing a minor amount of starting aldehyde, isovanillin.

EXAMPLE 13

A one liter glass reactor is charged with 3-hydroxy-4-methoxystyrene (60 g) (as prepared Example 12), a 4:1 mixture of 2,6 and 2,4-toluene dissocyanate (70 g) and phenothiazine (0.2 g). The stirred mixture is kept under a dry nitrogen atmosphere and heated to 50° C. Dibutyltin dilaurate (0.3 g) and triethylene diamine (0.2 g) are added. As the temperature increases, the reactor is cooled so as to maintain a maximum exotherm of 71° C. The temperature is then maintained at 65° for a further 1.5 hours after which time in infra-red spectrum of the mixture indicates complete consumption of the starting phenol. Tetraethylene glycol (77.6 g), dibutyltin dilaurate (0.1 g) and triethylene diamine (0.1 g) are then added. As the temperature increases, the reactor is again cooled so as to maintain the maximum exotherm at 75° C. The temperature is then maintained at 65° C. for two hours after which time the infra-red spectrum of the mixture shows no peak due to the isocyanate group. The reactor contents are cooled and a cationically cureable resin of the formula:

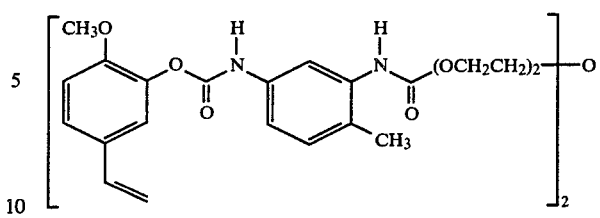

is obtained.

EXAMPLE 14

3-hydroxy-4-methoxystyrene (15 g) (as prepared by method described in Example 12), 1,4-dibromobutane (11.88 g) and phenothiazine (0.01 g) are dissolved in a stirred mixture of dry toluene (100 mls) containing potassium carbonate (20.7 g). Tetra-n-butylammonium bromide (3.22 g) is added and the mixture heated at 80° C. until the starting phenol has been consumed, as indicated by thin layer chromatography (approx. 3 hours). The mixture is cooled and filtered. The filtrate is washed with water (3×50 ml portions) and dried over sodium sulphate. After filtering the solvent is removed under reduced pressure to yield a cationically cureable compound of the formula:

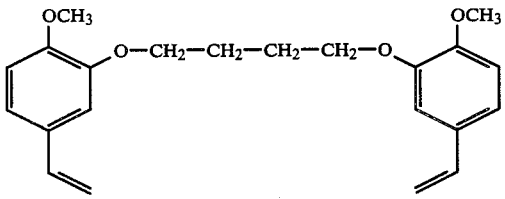

EXAMPLE 15

To a mixture of 1.5 equivalents K₂CO₃ dispersed in acetone is added 1.1 equivalents of 3-hydroxy-4-mextoxystyrene, sufficient polyvinyl chloride or vinylchloride co.polymer to provide approximately one equivalent of allylic chloride groups (i.e. —CH=CH—CH-Cl—) and 0.02% (by weight) phenothiazine. The mixture is refluxed for about four hours after which the inorganic salts are filtered and the polymer precipitated with hexane or petroleum spirit and dried. The resulting polymer, which has multiple groups within its backbone of the structure:

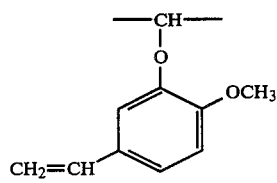

is cationically active.

EXAMPLE 16

Two equivalents of the monoethoxylate of isovanillin is reacted with 1 mole oxalylchloride followed by Wittig reaction on the aldehyde functionalities to give

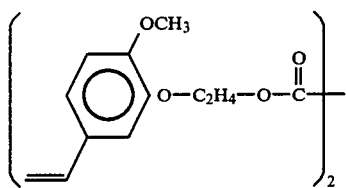

Other di or polyesters may be prepared by analogous procedures, using, for instance, sebacoyl chloride, phthaloylchloride, the tetrachloride of benzophenone tetracarboxylic acid, etc., or the corresponding acid anhydrides.

EXAMPLE 17

The monoethoxylate of isovanillin is esterified with 2-mercapto acetic acid followed by Wittig reaction to give a thiol functional styryloxy ester of the formula:

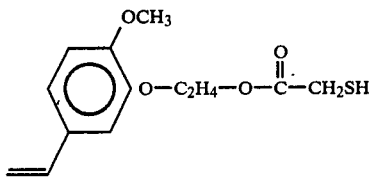

This thiol may then be reacted with a plural functional thiol reactive compound such as a di- or poly-isocyanate to give a multifunctional cationically cureable styryloxy resin.

EXAMPLE 18

Isovanillin is reacted with epichlorohydrin in the presence of potassium carbonate as etherification catalyst to give the glycidyl ether of isovanillin. This ether is polymerized cationically to give a polyether polymer, substantially free of hydroxyls, having repeat units of the formula:

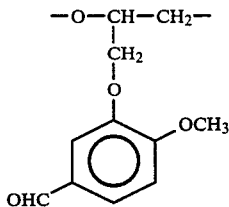

Wittig reaction on this polymer gives the corresponding cationically cureable styryloxy functional polyether.

EXAMPLE 19

The glycidyl ether of isovanillin is reacted with toluene diisocyanate in the presence of $ZnBr_2/(C_4H_9)_4PO$ catalyst at a ratio of 2 moles aldehyde to each mole diisocyanate under standard oxazolidone synthesis conditions followed by Wittig reaction on the aldehyde functionalities to give

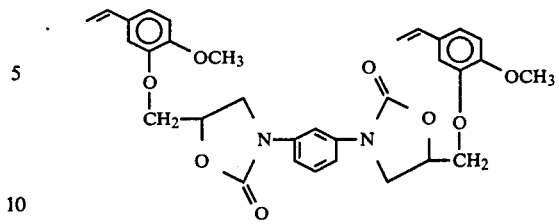

Similar resins can be prepared from other diisocyanate or polyisocyanate functional materials.

EXAMPLE 20

The monoethoxylate of isovanillin is reacted with a phosphazene polymer or cyclic oligomer having plural repeat units of the formula:

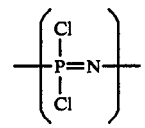

at a ratio of 2 equivalents of aldehyde per repeat unit of the formula above. The reaction is run in THF in the presence of a 10% molar excess (based on aldehyde content) of triethylamine in a sealed tube at 100° C. for 24 hours.

The ammonium chloride produced by the reaction is filtered from the cooled solution and the polymer isolated by evaporation of the solvent. The aldehyde functionality is then subjected to Wittig reaction to give a phosphazene polymer with plural units of the formula:

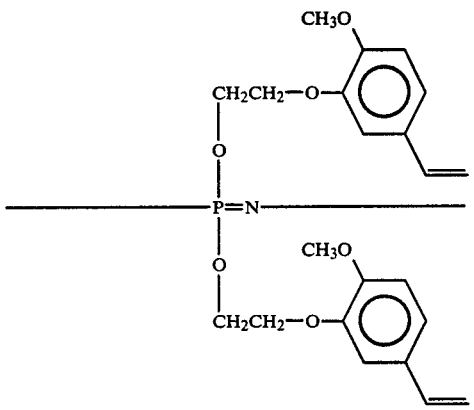

Other products of the invention having phosphazene backbones may also be prepared by methods which will be apparent to those skilled in the art, including copolymers in which some of the P-Cl bonds are substituted with another organic group before reaction with the ethoxylated benzaldehyde. Other benzaldehydes may also be used, for instance the monoethylenehydroxy group may be replaced by other alkylene hydroxy groups, the carbon atoms of which may be optionally interrupted with one or more oxygen atoms.

Aldehyde compounds of this type may be represented by the formula:

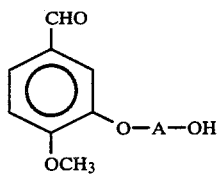

where A is alkylene, alkyleneoxy alkylene or (poly alkyleneoxy)alkylene.

We claim:

1. Polyfunctional cationically polymerizable styryloxy compounds of the formula

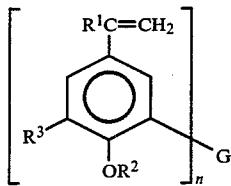

where $R^1$ is H or methyl; $R^2$ is hydrocarbyl, hydrocarbyl interrupted by ether oxygen atoms, or halo substituted hydrocarbyl; $R^3$ is H, lower alkyl, or alkoxy; G is any multivalent organic or inorganic radical free of amino or aliphatic thiol groups; and n is an integer of two or more.

2. A compound as in claim 1 wherein $R^1$ is H.

3. A compound as in claim 1 wherein $R^1$ is $CH_3$.

4. A compound as in claim 1 wherein $R^2$ is hydrocarbyl.

5. A compound as in claim 4 where $R^2$ is alkyl.

6. A compound as in claim 1 where $R^2$ is hydrocarbyl interrupted by one or more ether oxygen atoms.

7. A compound as in claim 1 where $R^2$ is halo substituted hydrocarbyl.

8. A compound as in claim 1 where $R^3$ is H.

9. A compound as in claim 1 comprising the addition reaction product of a compound of the formula

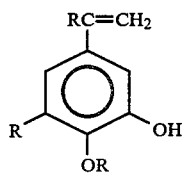

with a polyisocyanate.

10. A compound as in claim 1 comprising the etherification reaction product of a compound of the formula

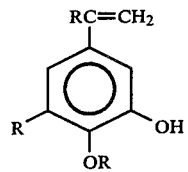

with a compound having plural haloalkyl functionality.

11. A compound as in claim 1 wherein G comprises a polyorganosiloxane backbone.

12. A compound as in claim 1 where G is selected from n-functional polyorganosiloxane, polyurethane, ppolyether, polyester, polythioether, polythioester, polyacrylic, polystyrene polyoxazolidone, polyimide hydrocarbon radicals.

13. A crosslinked polymer of a compound as in claim 1.

14. A polymer as in claim 13 crosslinked by UV irradiation of a solid compound as in claim 1 in the absence of a photoinitiator.

15. A polymer as in claim 13 crosslinked by cationic polymerization.

16. A polymer as in claim 15 wherein said polymer is obtained by UV irradiation of a composition comprising said styryloxy compound and a cationic photoinitiator.

17. A method of curing a compound to a cross-linked solid, the compound having the formula:

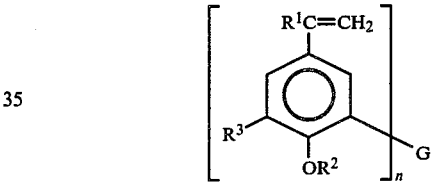

where $R^1$ is H or methyl; $R^2$ is hydrocarbyl, hydrocarbyl interrupted by oxygen atoms, or halo substituted hydrocarbyl; $R^3$ is H, lower alkyl, or alkoxy; G is any multivalent organic or inorganic radical free of amino or aliphatic thiol groups; and n is an integer of 7.

18. A method as in claim 17 for providing a colored cross-linked coating on a substrate, the method further comprising coating said substrate with said composition prior to cationically polymerizing the composition.

19. The method of claim 18 wherein said composition further comprises a cationic photoinitiator and said cationically polymerizing step comprises irradiating said composition coated substrate with UV irradiation.

20. The method of claim 19 wherein said cationic photoinitiator is a salt complex halogenide having the formula $[A]_b{}^+[MX_e]^{-(e-f)}$ where A is a cation selected from the group consisting of iodonium, sulfonium, thiopyrylium, pyrylium and diazonium cations, M is a metalloid, and X is a halogen radical, b equals e minus f, f equals the valence of M and is an integer equal to from 2-7 inclusive, e is greater than f and is an integer having a value up to 8.

* * * * *